US005889050A

United States Patent [19]

Andersson et al.

[11] Patent Number: 5,889,050
[45] Date of Patent: *Mar. 30, 1999

[54] 3,3'-DITHIOBIS (PROPIONIC ACIDS) AND ESTERS THEREOF

[75] Inventors: Carl-Magnus Alexander Andersson, Lund; Sten Håkan Axel Bergstrand, Bjärred; Anders Rudolf Hallberg, Lund; Bengt Olof Särnstrand, Bjärred; Per Anders Sigvard Tunek, Malmo, all of Sweden

[73] Assignee: Astra Aktiebolag, Sodertalje, Sweden

[ * ] Notice: The term of this patent shall not extend beyond the expiration date of Pat. No. 5,441,976.

[21] Appl. No.: 275,932

[22] Filed: Jul. 14, 1994

Related U.S. Application Data

[63] Continuation of Ser. No. 719,266, Jun. 21, 1991, abandoned.

[51] Int. Cl.$^6$ ............................................... A61K 31/255
[52] U.S. Cl. ............................................................ 514/517
[58] Field of Search ............................................ 514/517

[56] References Cited

U.S. PATENT DOCUMENTS

| | | | |
|---|---|---|---|
| 3,878,305 | 4/1975 | Damico et al. . | |
| 3,952,115 | 4/1976 | Damico et al. | 426/590 |
| 4,708,965 | 11/1987 | Morgan | 514/563 |
| 4,724,239 | 2/1988 | Morgan | 514/563 |
| 4,827,016 | 5/1989 | Morgan | 560/16 |
| 5,441,976 | 8/1995 | Aqndersson et al. . | |

FOREIGN PATENT DOCUMENTS

| | | |
|---|---|---|
| 0300100 | 1/1989 | European Pat. Off. . |
| 1462498 | 12/1966 | France . |
| 8205 | 9/1970 | France . |
| 2503151 | 4/1981 | France . |
| 8106592 | 10/1982 | France . |
| 2326444 | 12/1973 | Germany . |
| 2545194 | 4/1976 | Germany . |
| 62-195356 | 8/1987 | Japan . |
| 1468646 | 3/1977 | United Kingdom . |
| 2097256 | 11/1982 | United Kingdom . |

OTHER PUBLICATIONS

Barbe, et al., *Chemical Abstracts*, 98:40416v, p. 348 (1983).
Martin, 1969, *Journal of Medicinal Chemistry*, 12:950–53.
Schaad et al., 1975, *Journal of Medicinal Chemistry*, vol. 18, No. 4, pp. 344–351.
Bowman et al., 1981, *Tetraheron Letters*, vol. 22, No. 16, pp. 1551–1554.
Sjodin et al., 1989, *Biochemical Pharmacology*, vol. 38, No. 22, pp. 3981–3985.
Kahns et al., 1990, *International Journal of Pharmaceutics*, 62:193–205.
Stevenson, F.K. "Tumor Vaccines," FASEB 5: 2250–2257 1990.
Van Wauwe et al. "Review Article: On the Biochemical Mode of Action of Levamis le: an Update," J. Immunopharmac. 13: 3–9, 1991.
Rosenberg, S.A. "Immunotherapy of Cancer using Interleukin 2: Current Status and Future Prospects," Immunology Today 9: 58–62, 1988.
Scully et al. "Weekly Clinicopathological Exercises," The New England Journal of Medicine 322: 252–261, 1990.
Roitt et al. "Hypersensitivity–Type IV," Immunology 22.1–22.9., Churchill Livingston eds. Grover Med. Pub., London, N.Y. 1990.
Varela et al. "Second Generation Immune Networks," Immunology Today 12: 159–166, 1991.
Hadden, John W. "Immunotherapy of Human Immunodeficiency virus Infection," TIPS Reviews 12: 107–111, 1991.
Radermecker et al. "Increase in the Number and the Phagocytic Function of Guinea Pig Pulmonary and Peritoneal Macrophages Following Oral Administration of RU 417140, A Glycoprotein Extract from Klebsiella Pneumoniae," J. Immunopharmac 10: 913–917, 1988.
Paupe, Jean. "Immunotherapy with an Oral Bacterial Extract (OM–85 BC) for Upper Respiratory Infection," Respiration 58: 150–154, 1991.
Schaeffer et al. "Effect of an Immunostimulatory Substance of Klebsiella Pneumoniae on Inflammatory Responses of Human Granulocytes, Basophils and Platelets," Arzneim–Forsch Drug Res. 41: 815–820, 1991.
Anderson et al. "TH2 and 'TH2–like' Cells in Allergy and Asthma: Pharmacological Perspectives," Tips 15: 324–332. 1990.
Katz, David H. "The Allergic Phenotype: Manifestation of 'Allergic Breakthrough' and Imbalance in Normal 'Damping' of IgE Antibody Production," Immunological Rev. 41: 77–108, 1978.
Bergstrand et al. "Stimuli–induced Superoxide Radical Generation in Vitro by Human Alveolar Macrophages from Smokers: Modulation by N–Acetylcysteine Treatment in Vivo," Journal of Free Radicals in Biology & medicine 2: 119–127, 1986.
Kemp et al. "Templates for Intramolecular O,N–Acyl Transfer via cyclic Intermediates Derived from Mercury Derivatives of L–Cysteine: Progress toward a Mercury–Based Thiol Capture Strategy," J. Org. Chem. 54: 3853–3858, 1989.
Bowman te al. "Reactions of Thiolate Anions with 2–Substituted–2–Nitropropanes," Tetrahedro Letters 22: 1551–1554, 1981.
Devlin, Thomas M. "Lipid Metabolism I: Utilization and Storage of Energy in Lipid Form," Biochemistry Correlations 482–484. 1986.

*Primary Examiner*—Samuel Barts
*Attorney, Agent, or Firm*—White & Case LLP

[57] ABSTRACT

New 3,3'-dithiobis(propionic acids) and esters thereof with immunomodulating effect, processes for their preparation, pharmaceutical compositions containing them and methods of their pharmacological use.

10 Claims, No Drawings

3,3'-DITHIOBIS (PROPIONIC ACIDS) AND ESTERS THEREOF

This application is a continuation of application Ser. No. 07/719,266, filed Jun. 21, 1991 now abandoned.

FIELD OF THE INVENTION

The present invention relates to new cystine derivatives with immunomodulating activity, processes for their preparation, pharmaceutical compositions containing them and methods for their pharmacological use.

The object of the invention is to provide a cystine derivative with immunomodulating activity. Such a substance will be useful in the treatment of various diseases.

BACKGROUND OF THE INVENTION

N-Acetyl-L-cysteine is a compound widely used for treating chronic obstructive airway diseases/chronic bronchitis (for further references see Multicentre Study Group. Long-term oral acetylcysteine in chronic bronchitis. A double-blind controlled study. Eur. J. Respir. Dis. 1980, 61 (suppl. 111), 93–108; Boman, G., Bäcker, U., Larsson, S., Melander, B., and Wåhlander, L. Oral acetylcysteine reduces exacerbation rate in chronic bronchitis. Report of a trial organized by the Swedish Society for Pulmonary Disease. Eur. J. Respir. Dis. 1983, 64, 405–415; and British Thoracic Society Research Committee. Oral N-acetylcysteine and exacerbation rates in patients with chronic bronchitis and severe airway obstruction. Thorax 1985, 40, 832–835). The mechanism of action of the compound is not disclosed; its effect has been attributed to mucolytic properties (see Multicentre Study Group. Long-term oral acetylcysteine in chronic bronchitis. A double-blind controlled study. Eur. J. Respir. Dis. 1980, 61 (suppl. 111), 93–108; Boman, G., Bäcker, U., Larsson, S., Melander, B., and Wåhlander, L. Oral acetylcysteine reduces exacerbation rate in chronic bronchitis. Report of a trial organized by the Swedish Society for Pulmonary Disease. Eur. J. Respir. Dis. 1983, 64, 405–415; and British Thoracic Society Research Committee. Oral N-acetylcysteine and exacerbation rates in patients with chronic bronchitis and severe airway obstruction. Thorax 1985, 40, 832–835), antioxidant properties (see Aruoma, O. I., Halliwell, B., Hoey, B. M., and Butler, J. Free Radical Biol. Med. 1989, 6, 593–597), and also immunomodulating properties (see Bergstrand, H., Björnson, A., Eklund, A., Hernbrand, R., Eklund, A., Larsson, K., Linden M., and Nilsson, A. Stimuli-induced superoxide radical generation in vitro by human alveolar macrophages from smokers: Modulation by N-Acetylcysteine treatment in vivo. J. Free Radicals Biol. & Med. 2, 1986, 119–127).

Also known is N,N'-diacetyl-L-cystine. This compound has previously shortly been described in the patent literature as well as in the scientific literature (U.S. Pat. No. 4,827,016; EP 300100; U.S. Pat. No. 4,724,239; U.S. Pat. No. 4,708, 965; DE 2326444; Wilson, I. D., and Nicholson, J. K. Analysis of thiols and disulfides in Sulphur-containing drugs and related organic compounds. Chemistry, Biochemistry and Toxicology (ed L. A. Damani) Vol. 2A. Analytical, biochemical and toxicological aspects of sulphur xenobiochemistry. Ellis Horwood Series in Biochemical Pharmacology (Halstred Press: a division of John Wiley & Sons) Chichester 1989, p. 45; and Sjödin, K., Nilsson, E., Hallberg, A., and Tunek, A. Metabolism of N-Acetyl-L-cysteine. Some structural requirements for the deacetylation and consequences for the oral bioavailability. Biochem. Pharmacol. 1989, 38, 3981–3985). In U.S. Pat. No. 4,827, 016 the compound is claimed to be effective for topical treatment of dermal inflammations which are induced and propagated by leukotrienes. However, nothing has been reported or generally known regarding its pharmacological and/or therapeutic properties with respect to immunological systems and inflammatory diseases of the lung such as chronic bronchitis.

Previously, immunostimulating properties have been reported for simple disulfides such as hydroxyethyldisulfide (HEDS, see: St. Georgiev, V. New synthetic immunomodulating agents. Trends in Pharmacological Science 1988, 446–51).

DISCLOSURE OF THE INVENTION

According to the present invention it has been found that a compound of the general formula

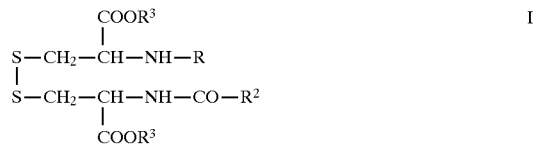

wherein R is hydrogen or a moiety —CO—R$^1$ wherein R$^1$ is methyl, ethyl, n-propyl, n-butyl, n-pentyl, n-hexyl, n-heptyl, n-octyl, n-nonyl, n-decyl, n-undecyl, iso-propyl, 1-methylpropyl, tert. butyl, 3-methylbutyl or 2-methylbutyl, R$^2$ is methyl, ethyl, n-propyl, n-butyl, n-pentyl, n-hexyl, n-heptyl, n-octyl, n-nonyl, n-decyl, n-undecyl, iso-propyl, 1-methylpropyl, tert. butyl, 3-methylbutyl or 2-methylbutyl, and R$^3$ is hydrogen, methyl, ethyl, propyl, isopropyl, butyl or isobutyl, provided that R$^1$ and R$^2$ are not simultaneously methyl and further provided that when R$^3$ is hydrogen R$^1$ and R$^2$ are not simultaneously n-propyl or n-heptyl, or a physiologically acceptable salt and/or a stereochemical isomer thereof, is an immunomodulating, particularly immunostimulating, agent.

Therefore, the compounds of the invention may be used for treatment of diseases where a defect in the immune system and/or an ineffective host defence is at hand or can be suspected.

Examples of such diseases are chronic bronchitis and other inflammatory diseases of the airways such as asthma and rhinitis but also certain forms of autoimmune diseases like diabetes and rheumatoid arthritis and/or various malignant diseases. HIV-infection or full blown AIDS may be treated with the compounds. Also atherosclerotic disease may be treated with the compounds.

Effective amounts of the compounds of the invention for use in the treatment of the above mentioned diseases are in the range 0.5–500 mg, preferably 5–50 mg, daily dose.

Preferred compounds of the formula I above are those wherein R is hydrogen or a moiety —CO—R$^1$ wherein R$^1$ is methyl, ethyl, n-propyl, n-butyl, n-pentyl, n-hexyl, n-heptyl, n-octyl, n-nonyl, n-decyl, n-undecyl, iso-propyl, 1-methylpropyl, tert. butyl, 3-methylbutyl or 2-methylbutyl, R$^2$ is methyl, ethyl, n-propyl, n-butyl, n-pentyl, n-hexyl, n-heptyl, n-octyl, n-nonyl, n-decyl, n-undecyl, iso-propyl, 1-methylpropyl, tert. butyl, 3-methylbutyl or 2-methylbutyl, and R$^3$ is hydrogen, methyl or ethyl, provided that R$^1$ and R$^2$ are not simultaneously methyl and further provided that when R$^3$ is hydrogen R$^1$ and R$^2$ are not simultaneously n-propyl or n-heptyl.

Preferred compounds of the formula I when R$^3$ is hydrogen are those wherein R$^1$ and R$^2$ are simultaneously iso-propyl and tert. butyl, respectively.

Preferred compounds of the formula I above when R$^3 \neq$ hydrogen are those where R$^1$ and R$^2$ contain 3–7 carbon atoms.

Particularly, preferred compounds of the formula I above when $R^3 \neq$ hydrogen are those where $R^1$ and $R^2$ are isopropyl and $R^3$ is methyl; $R^1$ and $R^2$ are n-pentyl and $R^3$ is methyl; $R^1$ and $R^2$ are n-heptyl and $R^3$ is methyl or ethyl.

The stereoisomeric form of the compounds of the invention particularly preferred is the L-isomer, i.e. compounds derived from L-cystine.

A physiologically acceptable salt of the compounds of formula I when $R^3$ is hydrogen is e.g. a salt of sodium, ammonium, calcium or magnesium, together with the non-toxic acid addition salts thereof. Also included are salts derived from arginine, lysine, histidine, ethanolamine, diethanolamine, ethylenediamine and choline, or other suitable organic amines.

A physiologically acceptable salt of the compounds of the formula I when $R^3 \neq$ hydrogen and R=hydrogen is the hydrochloride, hydrobromide, hydrosulphate, oxalate, tartrate etc. The salts may also be in the form of solvates, e.g. hydrates.

PHARMACEUTICAL FORMULATIONS

The described active substances can be included in different dosage forms e.g. tablets, coated tablets, gelatin capsules, solutions and aerosols.

For the preparation of tablets, coated tablets and gelatin capsules the active substance can be combined with pharmaceutically acceptable materials, e.g. lactose, starch, dicalcium phosphate, microcrystalline cellulose, polyvinylpyrrolidone, gelatin, cellulose derivatives, colloidal silicone dioxide, talc and stearic acid or its salts.

For the preparation of oral solutions suitable excipients are water, saccharose, glucose, sorbitol, fructose and xylitol.

The dosage forms can besides mentioned excipients contain preservatives, stabilizers, viscosity regulating agents, emulsifiers, sweetening agents, coloring agents, flavoring agents, tonicity regulating agents, buffers or antioxidants. They can also contain other therapeutically valuable substances.

METHODS OF PREPARATION

The compounds of the invention may be obtained by any of the following methods:

A. The oxidation of an N-acylcysteine derivative of the formula

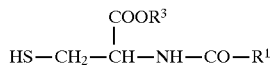

wherein $R^1$ and $R^3$ are as defined above or when $R^3$ is hydrogen optionally salt thereof, to the formation of a compound of the formula

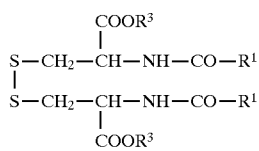

As oxidant may be used:

Hydrogen peroxide, air under alkaline conditions, alkylhydroperoxides, peracids, a halogen, nitrous or nitric oxide, oxidizing metals such as thallium (III), trialkylsulfonium salts, or selenium or tellurium oxides. The oxidation can also be performed electrochemically.

A halogen is for instance chlorine, bromine or iodine. As salts in method A and the following may be used: sodium, potassium, calcium, ammonium etc.

B. The reaction, in the presence of a suitable base, of a compound having the formula

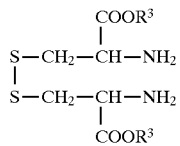

or a salt thereof wherein $R^3$ is as defined above, with a compound of the formula

wherein $R^1$ is defined as above and COX is a reactive group capable of reacting with an amino group under formation of an amide moiety, to the formation of a compound of the formula

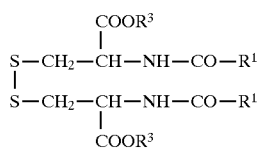

The acylating agent $R^1COX$ can for instance be an acid halide, anhydride, an amide, or an activated acid or ester.

A salt in method B and in any following methods where a salt can be used can be an hydrochloride, hydrobromide, hydrosulphate, oxalate, tartrate etc. A salt in method B can also be any of the alkali salts mentioned in method A.

C. The reaction of a 2-(N-acylamino)-3-halopropionic acid derivative of the formula

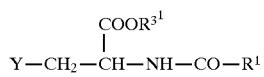

wherein $R^1$ is as defined above, $R^{3^1}$ is $R^3$ as defined above or an acid or base labile organic group and Y is a halogen atom, with sulphur or disulphide dianion in the presence of a base, to the formation of a compound of the formula

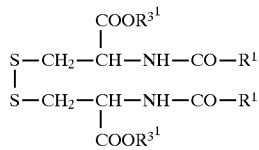

whereafter, if a compound wherein $R^3=H$ is derived, removal of the protecting group $R^{3^1}$ The protecting group, $R^{3^1}$, may be an acid or base labile organic group such as an alkyl, benzyl, aryl, vinyl or an allyl group.

D. The oxidation of a mixture of N-acylcysteine derivatives of the formulas

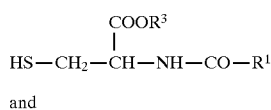

and

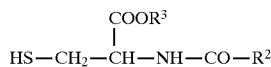

wherein $R^1$, $R^2$ and $R^3$ are as defined above or when $R^3$ is hydrogen optionally alkali salts thereof, to the formation of a compound of the formula

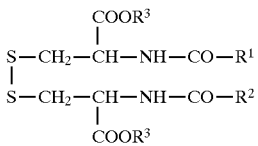

The oxidising agents of method A are applicable.

E. The oxidation of a mixture of cysteine or a cysteine ester and an N-acylcysteine derivative of the formulas

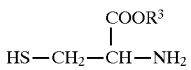

or a salt thereof
and

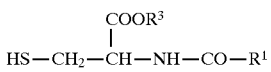

or alkali salts thereof, wherein $R^1$ and $R^3$ are as defined above, to the formation of a compound of the formula

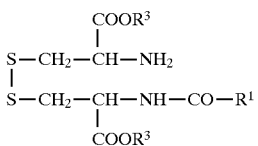

or a salt thereof.

The oxidising agents of method A may be used.

F. The reaction, in the presence of a suitable base, of an excess of cystine or a cystine diester having the formula

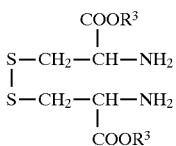

or a salt thereof wherein $R^3$ is as defined above, with a compound of the formula

wherein $R^2$ and COX are as defined above, to the formation of a compound of the formula

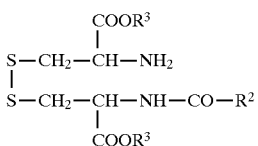

G. The reaction, in the presence of a suitable base, of a compound of the formula

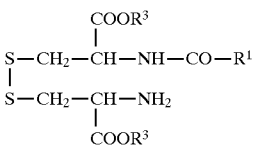

or a salt thereof wherein $R^1$ and $R^3$ are as defined above, with a compound of the formula

wherein $R^2$ and COX are as defined above, to the formation of a compound of the formula

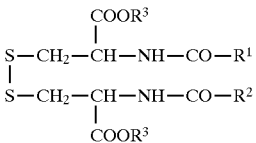

H. The reaction of an N-acylcysteine derivative of the formula

or a salt thereof with an activating reagent such as diethylazodicarboxylate to give an adduct of e.g. the formula

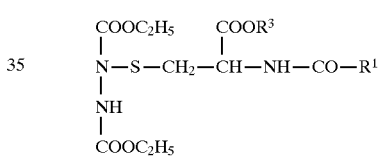

followed by reaction with a second, different or the same N-acylcysteine or N-acylcysteine ester to give a compound of the formula

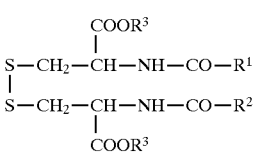

I. The reaction of a compound of the formula

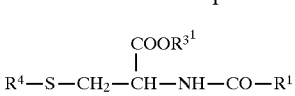

wherein $R^4$ is

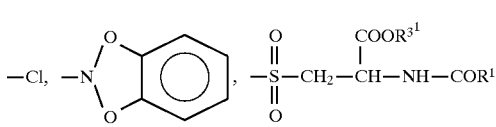

and
$R^1$ and $R^{3^1}$ are as defined above, with a compound of the formula

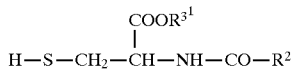

wherein $R^2$ and $R^{3^1}$ are as defined above to the formation of a compound of the formula

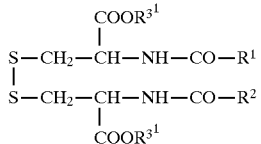

whereafter, if a compound wherein $R^3$=H is desired, removal of the protecting group $R^{3^1}$.

J. The esterification of a compound of the formula

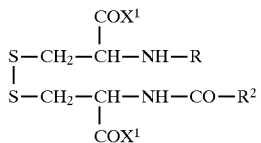

wherein R and $R^2$ are as defined above and $X^1$ is OH or a halogen atom, with a compound of the formula

wherein $R^{3E}$ is methyl, ethyl propyl, isopropyl, butyl or isobutyl, to the formation of a compound of the formula

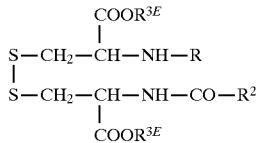

K. The alkylation of a compound of the formula

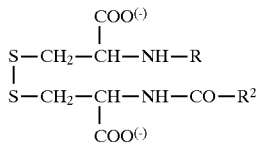

wherein R and $R^2$ are as defined above, with a compound of the formula

wherein $R^{3E}$ is as defined above and Z is a halide, alkylsulphate, tosylate or another nucleofuge to the formation of a compound of the formula

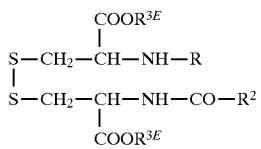

L. The reaction, in the presence of a suitable base, of a carboxyl protected cystine derivative of the formula

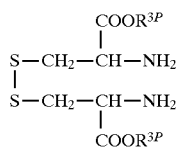

or a hydrochloride salt thereof, wherein $R^{3P}$ is an acid or base labile organic group, with a compound of the formula

wherein $R^1$ is defined as above and COX is a reactive group capable of reacting with an amino group under formation of an amide moiety, and thereafter removal of the protecting group $R^{3P}$ to the formation of a compound of the formula

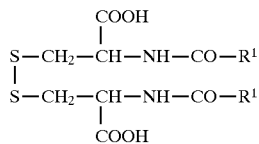

The acylating agent $R^1$COX is as defined under B. The protecting group, $R^{3P}$, may be an acid or base labile organic group such as an alkyl, benzyl, aryl, vinyl or allyl group.

M. The reaction, under alkaline conditions, of a carboxyl protected cystine derivative of the formula

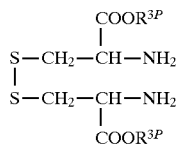

or a hydrochloride salt thereof, wherein $R^{3P}$ is as defined above, with a compound of the formula $R^2$—COX wherein $R^2$ and COX are as defined above and thereafter removal of the protecting group $R^{3P}$ to the formation of a compound of the formula

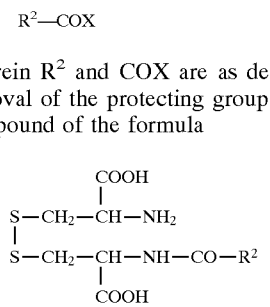

N. The reaction of a carboxyl protected cystine derivative of the formula

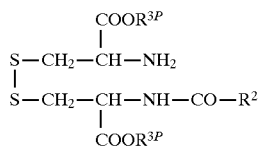

or a hydrochloride salt thereof, wherein $R^2$ and $R^{3P}$ are as defined above, with a compound of the formula

wherein R¹ and COX are as defined above and thereafter removal of the protecting group $R^{3P}$ to the formation of a compound of the formula

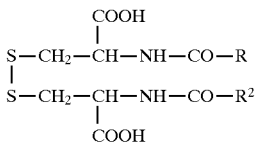

O. The equilibration, in alcohol or aqueous solution, of a mixture of a cystine derivative and a cysteine derivative having the formulas

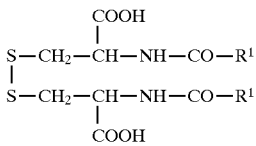

and

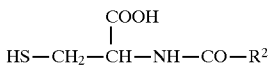

or alkali salts thereof, wherein R¹ and R² are as defined above, to the formation of a compound of the formula

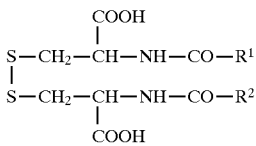

An optional step in all methods A–O is transferring of the obtained compound into a physiologically acceptable salt.

WORKING EXAMPLES

Example 1

(R,R)-N,N'-dipentanoyl-3,3'-dithiobis(2-aminopropionic acid)dimethylester

A suspension of L-cystinedimethylester dihydrochloride (1.0 g, 3 mmol) in THF (20 mL) (white slurry) was stirred and cooled to 0° C. To the reaction mixture was added 4 equiv. (2.0 mL) of N-ethyldiisopropylamine and 2.2 equiv. (0.8 mL, 6.6 mmol) of pentanoylchloride. The mixture was stirred for 4 h on the ice-bath and the white precipitate of N-ethyldiisopropylammonium chloride was removed by filtration. The solvent was removed by evaporation and the crude product was redissolved in dichlormethane. After washing with water the organic phase was dried over sodium sulphate. Filtration and evaporation of the solvent gave the crude title product, which was recrystallised from ethyl acetate.

Physical data: $^1$H-NMR (300 MHz, CDCl$_3$): δ 6.42 (2H, d, NH), 4.88 (2H, dt, NCH), 3.77 (6H, s, OCH$_3$), 3.21 (4H, m, SCH$_2$), 2.27 (4H, t, COCH$_2$), 1.63 (4H, m, CH$_3$CH$_2$CH$_2$), 1.36 (4H, m, CH$_3$CH$_2$), 0.92 (6H, t, CH$_3$). $\alpha_D^{25}$=−146° (C=0,490, MeOH). Mp=110°–112° C. Anal. Calcd for C$_{18}$H$_{32}$O$_6$N$_2$S$_2$: C, 49.52; H, 7.39; N, 6.42; S, 14.69. Found: C, 49.40; H, 7.40; N, 6.40; S, 14.70.

Example 2

(R,R)-N,N'-dipropionyl-3,3'-dithiobis(2-aminopropionic acid)dimethylester

The compound was prepared according to the procedure described in Example 1 using propionylchloride as acylating reagent.

Physical data: $^1$H-NMR (300 MHz, CDCl$_3$): δ 6.44 (2H, d, NH), 4.89 (2H, dt, NCH), 3.78 (6H, s, OCH$_3$), 3.22 (4H, m, SCH$_2$), 2.31 (4H, q, CH$_3$CH$_2$CH$_2$), 1.18 (6H, t, CH$_3$).

Example 3

(R,R)-N,N'-dipentanoyl-3,3'-dithiobis(2-aminopropionic acid)diethylester

The compound was prepared according to the procedure described in Example 1 starting from L-cystinediethylester dihydrochloride and using pentanoylchloride as acylating reagent.

Physical data: $^1$H-NMR (300 MHz, CDCl$_3$): δ 6.43 (2H, d, NH), 4.85 (2H, dt, NCH), 4.23 (4H, m, OCH$_2$), 3.22 (4H, m, SCH$_2$), 2.27 (4H, t, COCH$_2$), 1.63 (6H, m, CH$_3$CH$_2$CH$_2$), 1.37 (4H, m, CH$_3$CH$_2$), 1.30 (6H, t, OCH$_2$CH$_3$, 0.92 (6H, t, CH$_3$). $\alpha_D^{28}$=−130° (C=0.514, MeOH). Mp=109° C. Anal. Calcd for C$_{20}$H$_{36}$O$_6$N$_2$S$_2$: C, 51.70; H, 7.81; N, 6.03; S, 13.80. Found: C, 51.85; H, 7.75; N, 6.10; S, 13.60.

Example 4

(R,R)-N,N'-dipropionyl-3,3'-dithiobis(2-aminopropionic acid)diethylester

The compound was prepared according to the procedure described in Example 1 starting from L-cystine diethylester dihydrochloride and using propionylchloride as acylating reagent.

Physical data: $^1$H-NMR (300 MHz, CDCl$_3$): δ 6.44 (2H, d, NH), 4.86 (2H, dt, NCH), 4.23 (4H, m, OCH$_2$), 3.22 (4H, m, SCH$_2$), 2.31 (4H, q, COCH$_2$), 1.30 (6H, t, CO$_2$CH$_2$CH$_3$, 1.18 (6H, t, CH$_3$).

Example 5

(R,R)-N,N'-dihexanoyl-3,3'-dithiobis(2-aminopropionic acid)diethylester

The compound was prepared according to the procedure described in Example 1 starting from L-cystinediethylester dihydrochloride and using hexanoylchloride as acylating reagent.

Physical data: $^1$H-NMR (300 MHz, CDCl$_3$): δ 6.44 (2H, d, NH), 4.86 (2H, dt, NCH), 4.23 (4H, m, OCH$_2$), 3.21 (4H, m, SCH$_2$), 2.26 (4H, t, COCH$_2$), 1.65 (4H, m, COCH$_2$CH$_2$), 1.31 (4H, m, CH$_3$CH$_2$CH$^2$, 1.31 (4H, m, CH$_3$CH$_2$), 1.31 (6H, t, OCH$_2$CH$_3$), 0.90 (6H, t, CH$_3$).

Example 6

(R,R)-N,N'-di(2-methylpropionyl)-3,3'-dithiobis(2-aminopropionic acid)diethylester The compound was prepared according to the procedure described in Example 1 starting from L-cystinediethylester dihydrochloride and using 2-methylpropanoylchloride as acylating reagent.

Physical data: $^1$H-NMR (300 MHz, CDCl$_3$): δ 6.42 (2H, d, NH), 4.84 (2H, dt, NCH), 4.23 (4H, m, OCH$_2$), 3.22 (4H, m, SCH$_2$), 2.46 (2H, m, (CH$_3$)$_2$CH), 1.30 (6H, t, OCH$_2$CH$_3$), 1.18 (12H, d, (CH$_3$)$_2$). $\alpha_D^{25}$=−127°(C=0,512, MeOH). Mp=140°–141° C. Anal. Calcd for C$_{18}$H$_{32}$O$_6$N$_2$S$_2$: C, 49.52; H, 7.39; N, 6.42; S, 14.69. Found: C, 49.15; H, 7.40; N, 6.30; S, 14.75.

Example 7

(R,R)-N,N'-di(1-oxo-dodecanyl)-3,3'-dithiobis(2-aminopropionic acid) dimethylester The compound was prepared according to the procedure described in Example 1, starting from (R,R)-3,3'-dithiobis (2-aminopropionic acid) dimethylester dihydro chloride and using dodecanoic acid chloride as the acylating agent.

Total yield: 40%; Physical data: Mp=98°–99° C. $[\alpha]_D^{25}$= –93° (c=0.531, MeOH). $^1$H-NMR (300 MHz CDCl$_3$) δ 6.42 (2H, d, NH) 4.88 (2H, dt, NCH) 3.77 (6H, s, OCH$_3$) 3.21 (4H, m, SCH$_2$) 2.26 (4H, t, OCH$_2$), 1.64 (4H, m, OCH$_2$CH$_2$), 1.26 (32H, m, (CH$_2$)$_8$), 0.88 (6H, t, CH$_2$CH$_3$). Anal. Calcd for C$_{32}$H$_{60}$N$_2$O$_6$S$_2$: C, 60.72; H, 9.56; N, 4.43; S, 10.13. Found: C, 60.4; H, 9.3; N, 4.5; S 10.1

Example 8

(S,S)-N,N'-di(2-methylpropionyl)-3,3'-dithiobis(2-aminopropionic acid)dimethylester N,N'-diisobutyryl-D-cystine (1.86 g, 4.9 mmol) was dissolved in 10 ml of methanol containing one drop of hydrochloric acid. Trimethylorthoformate (0.6 ml, 5.5 mmol) was added and the reaction mixture was stirred at room temperature for 4 days. After evaporation of the solvent, the product was purified by column chromatography (solvent heptane:ethyl acetate 1:5).

Physical data: Mp 145.5°–147.5° C. $^1$H-NMR (300 MHz CDCl$_3$) δ 6.39 (2H, d, NH) 4.86 (2H, dt, NCH) 3.78 (6H, s, OCH$_3$) 3.21 (4H, m, SCH$_2$) 2.47 (2H, h, CH(CH$_3$)$_2$) 1.18 (12H, d, CH(CH$_3$)$_2$. $[\alpha]_D^{25}$=+135,2 (C=0.42, MeOH)

Example 9

(R,R)-N,N'-dihexanoyl-3,3'-dithiobis(2-aminopropionic acid)dimethylester

The compound was prepared according to the procedure described in Example 1 using hexanoylchloride as acylating reagent.

Physical data: $^1$H-NMR (300 MHz, CDCl$_3$): δ 6.41 (2H, d, NH), 4.88 (2H, dt, NCH), 3.76 (6H, s, OCH$_3$), 3.21 (4H, m, SCH$_2$), 2.26 (4H, t, COCH$_2$), 1.65 (4H, q, CH$_3$CH$_2$CH$_2$CH$_2$), 1.33 (4H, m, CH$_3$CH$_2$, 1.33 (4H, m, CH$_3$CH$_2$), 0.89 (6H, t, CH$_3$). $\alpha_D^{25}$=–135°(C=0,486,MeOH). Mp=90°–92° C. Anal. Calcd for C$_{20}$H$_{36}$N$_2$O$_6$S$_2$: C, 51.70; H, 7.81; N, 6.03; S, 13.80. Found: C, 51.90; H, 7.95; N, 6.10; S, 13.75.

Example 10

(R,R)-N,N'-di(1-oxo-octyl)-3,3'-dithiobis (2-aminopropionic acid)dimethylester

The compound was prepared according to the procedure described in Example 1 using octanoylchloride as acylating reagent.

Physical data: $^1$H-NMR (300 MHz, CDCl$_3$): δ 6.41 (2H, d, NH), 4.88 (2H, dt, NCH), 3.77 (6H, s, OCH$_3$), 3.21 (4H, m, SCH$_2$), 2.26 (4H, t, COCH$_2$), 1.65 (4H, t, COCH$_2$CH$_2$), 1.29 (16H, m, CH$_3$(CH$_2$)1–4), 0.88 (6H, t, CH$_2$CH$_3$). $\alpha_D^{25}$= –119°(C=0,490, MeOH). Mp=90°–91° Anal. Calcd for C$_{24}$H$_{44}$N$_2$O$_6$S$_2$: C, 55.36; H, 8.52; N, 5.38; S, 12.31. Found: C, 54.80; H, 8.45; N, 5.35; S, 11.80.

Example 11

(R,R)-N,N'-di(1-oxo-octyl-3,3'-dithiobis(2-aminopropionic acid)diethylester

The compound was prepared according to the procedure described in Example 1 starting from L-cystinediethylester dihydrochloride and using octanoylchloride as acylating reagent.

Physical data: $^1$H-NMR (300 MHz, CDCl$_3$): δ 6.43 (2H, d, NH), 4.85 (2H, dt, NCH), 4.23 (4H, m, CH$_3$CH$_2$O), 3.21 (4H, m, SCH$_2$), 2.26 (4H, t, COCH$_2$), 1.65 (4H, t, COCH$_2$CH$_2$), 1.30 (6H, m, OCH$_2$CH$_3$), 1.30 (16H, m, CH$_3$(CH$_2$)1–4), 0.88 (6H, t, CH$_2$CH$_3$).

Example 12

(R,R)-N,N'-di(2,2-dimethylpropionyl)-3,3'-dithiobis (2-aminopropionic acid)diethylester The compound was prepared according to the procedure described in Example 1 starting from L-cystinediethylester dihydrochloride and using 2,2-dimethylpropanoylchloride as acylating reagent.

Physical data: $^1$H-NMR (300 MHz, CDCl$_3$): δ 6.52 (2H, d, NH), 4.80 (2H, dt, NCH), 4.22 (4H, m, CH$_3$CH$_2$O), 3.22 (4H, m, SCH$_2$), 1.30 (6H, t, OCH$_2$CH$_3$), 1.23 (18H, s, C(CH$_3$)$_3$).

Example 13

(R,R)-N,N'-di(2,2-dimethylpropionyl)-3,3'-dithiobis (2-aminopropionic acid)dimethylester The compound was prepared according to the procedure described in Example 1 using 2,2-dimethylpropanoylchloride as acylating reagent.

Physical data: $^1$H-NMR (300 MHz, CDCl$_3$): δ 6.51 (2H, d, NH), 4.83 (2H, dt, NCH), 3.78 (6H, s, OCH$_3$), 3.21 (4H, m, SCH$_2$), 1.23 (18H, S, C(CH$_3$)$_3$).

Example 14

(R,R)-N,N'-di(2-methylpropionyl)-3,3'-dithiobis(2-aiminopropionic acid)dimethylester The compound was prepared according to the procedure described in Example 1 but with 2-methylpropionyl chloride replacing pentanoyl chloride.

Physical data: Mp 142°–5° C. δ 6.40 (2H,d,NH), 4.86 (2H,dt, NCH), 3.78(6H, s, OCH$_3$), 3.21 (4H,m,SCH$_2$), 2.47 (2H,h,CH(CH$_3$)$_2$), 1.18(12H,d,CH(CH$_3$)$_2$).

Example 15

(R,R)-N-acetyl-N'-hexanoyl-3,3'-dithiobis-(2-aminopropionic acid)dimethylester (R,R)-3,3'-dithiobis(2-aminopropionic acid)dimethylester dihydrochloride (690 mg, 2 mmol) was stirred together with 1.39 ml (10 mmol) of triethylamine in 20 mL of THF in a 100 mL round bottomed flask. The turbid solution was cooled to 0° C. on an ice bath before a solution of acetyl chloride (142 μL, 2 mmol) and hexanoylchloride (276 μL, 2 mmol) in 3 mL of THF was added dropwise. The turbid solution was stirred for 1 h at 0° C. A white precipitate of 1 g (100%) Et$_3$NHCl was filtered off and the filtrate was evaporated to give an oily residue, which was partitioned between 10 mL of H$_2$O and 10 mL of CHCl$_3$. After separating the phases, the aqueous phase was extracted with 3×10 mL of CHCl$_3$. After evaporating the combined CHCl$_3$-phases the crude product (containing the desired product and the symmetrical derivatives) was separated by Flash chromatography according to Still et al. (J. Org. Chem., 1978, 43, 2923) on silica gel 60 (E. Merck 5735, 230–400 mesh ASTM), with EtOAc/Heptane/MeOH 6:3:1 as the eluent. The separation was monitored by thin layer chromatography (plastic sheets silica gel 60 WF$_2$54s, E. Merck 16483, with EtOAc/Heptane/MeOH 6:3:1 as eluent and $I_2$ as visualization agent). The fractions with acceptable purity were pooled and evaporated to give an oily residue. This residue was dissolved in acetone and the solution was again evaporated to give the title product as a colorless solid.

Yield 184 mg, 25%. Physical data: TLC: $R_f$=0.30 (EtOAc/Heptane/MeOH=6/3/1). $^1$H-NMR (300 MHz, CDCl$_3$): δ 6.53 (1H, d, NH), 6.43 (1H, d, NH), 4.88 (2H, m, NCH), 3.78 (6H, s, CO$_2$CH$_3$), 3.22 (4H, m, SCH$_2$), 2.26 (2H, t, COCH$_2$), 2.07 (3H, s, COCH$_3$), 1.65 (2H, m, CH$_2$), 1.32 (4H, m, CH$_2$), 0.90 (3H, t, CH$_3$). FAB-MS (m/z): 431 [MNa], $^+$409 [MH]$^+$, 311 [MH-C$_7$H$_{11}$O]$^+$.

Example 16

(R,R)-N,N'-di(2-methylpropionyl)-3,3'-dithiobis(2-aminopropionic acid)

N-Isobutyryl-L-cysteine (9.5 g, 50 mmol) was dissolved in 50 mL of water. Hydrogen peroxide (30%, 3.1 mL, 30 mmol) was added and the reaction mixture was stirred at room temperature for 6 hours. After evaporation of the solvent under reduced pressure, a white crystallised oil (9.8 g) was obtained. Recrystallisation from ethyl acetate furnished the title compound as a white solid which was dried in vacuo.

Yield: 4.8 g (50%). Physical data: Mp. 143°–5° C.; $^1$H-NMR (300 MHz, DMSO-d$_6$), δ (2H, b, CO$_2$H), 8.16 (2H, d, NH), 4.47 (2H, m, CHN), 3.15 (2H, dd, CH$_2$S, J=14 Hz, 5 Hz), 2.92 (2H, dd, CH$_2$S, J=14 Hz, 9 Hz), 2.43 (2H, h, CH(CH$_3$)$_2$, J=7 Hz), 1.01 (12H, d, CH$_3$, J=7 Hz). [δ]$_d^{25}$= –169.8 (MeOH, C=0.510)

Example 17

(R,R)N-Acetyl-3,3'-dithiobis(2-aminopropionic acid)

L-cysteine (2.42 g, 20 mmol) and N-acetyl-L-cysteine (3.26 g, 20 mmol) were dissolved in 25 mL of water. The pH of this solution was 2.6 according to lithmus paper. Aqueous hydrogen peroxide (30%, 2.3 mL, 21 mmol) was added, and the reaction mixture was allowed to stand at room temperature overnight. A white precipitate stand at room temperature overnight. A white precipitate was filtered off (1.26 g). This material was shown to be L-cystine by comparison of spectral data with an authentic sample. The yellowish filtrate, containing the desired compound and the two symmetrical compounds (R,R)-N,N'-diacetylcystine and (minor amounts of) cystine was separated on a preparative HPLC using a Dynamax C$_1$8-column (8 μm, 60 Å, 21.4×250 mm) with a Dynamax C$_1$8-guard column (8 μm, 21.4×50 mm) and with Gilson dual solvent delivery system (305 pump, pumphead 100 SC acting as a solvent delivery pump, pumphead 5 SC acting as a sample injector, 806 manometric module, 811B dynamic mixer, 115 UV detector, 201 fraction collector, 201–202 fraction controller). The solvents used were A=10 mM HOAc/H$_2$O and B=MeOH, with a 95:5 ratio of A:B. The solvent flow was 10 mL/min and the separation was recorded at 230 nm. After detection of each fraction on TLC (Merck 16483, plastic sheets silica gel 60 WF 254s, eluent "BuOH/HOAc/H$_2$O 1:1:1, $I_2$ as visualization agent), the fractions with acceptable purity were pooled and evaporated to give an oily residue. This residue was dissolved in acetone (pa) and the solution was evaporated to give the title product as white crystals.

Yield: 10%. Physical data: TLC: $R_f$=0.69 ("BuOH/HOAc/H$_2$O=1/1/1). $^1$H-NMR (300 MHz, D$_2$O): δ 4.73 (1H, dd, NCH), 4.18 (1H, dd, NCH), 3.37 (2H, m, SCH$_2$), 3.10 (2H, m, SCH$_2$), 2.06 (3H, s, CH$_3$). TSP-MS (m/z): 283 [MH]$^+$, 164 [MH-C$_3$H$_5$NO$_2$]$^+$.

Example 18

(R,R)-N-Acetyl-N'-(2-methylpropionyl)-3,3'-dithiobis(2-aminopropionic acid)

A mixture of N-acetyl-L-cysteine (0.652 g, 4 mmol) and N-isobutyryl-L-cysteine (0.764 g, 4 mmol) in 10 mL of MeOH was stirred while hydrogen peroxide (30%, 0.60 mL, 5 mmol) was added dropwise. The stirring was continued for 3 hours at room temperature, after which the solvent was removed on the rotary evaporator. Addition of 25 mL of acetone and repeated evaporation afforded 1.5 g of crude material as an oil which solidified on standing. The desired title compound was isolated from this mixture by preparative HPLC as described in Example 17.

Yield: 31%. Physical data: HPLC elution with 60% A (isocratic, for solvents see Example 17). TLC: $R_f$=0.76 ("BuOH/H$_2$/HOAc=1/1/1). $^1$H-NMR (300 MHz, D$_2$O): δ 4.73 (2H, m, NCH), 3.33 (2H, m, SCH$_2$), 3.03 (2H, m, SCH$_2$), 2.59 (1H, n, H), 2.06 (3H, s, COH$_3$), 1.13 (3H, d, CH$_3$), 1.11 (3H, s, CH$_3$). FAB-MS (m/z): 376 [MNa]$^+$, 353 [MH]$^+$.

Example 19

(R,R)-N-(2-methylpropionyl)-3,3'-dithiobis (2-aminopropionic acid)

The compound was prepared by the procedure given in Example 17, starting from L-cysteine and N-isobutyryl-L-cysteine.

Yield: 8%. Physical data: HPLC elution with 55% A (isocratic, see Example 17 for solvents). TLC: $R_f$=0.67 "BuOH/H$_2$O/HOAc=1/1/1). $^1$H-NMR (300 MHz, D$_2$O): δ 4.73 (1H, dd, NCH), 4.14 (1H, dd, NCH), 3.38 (2H, n, SCH$_2$), 3.08 (2H, m, SCH$_2$), 2.06 (1H, n, CH), 1.15 (3H, d, CH$_3$), 1.13 (3H, d, CH$_3$). TSP-MS (m/z): 311 [MH]$^+$.

Example 20

(R,R)-N-Acetyl-N'-(2,2-dimethylpropionyl)-3,3'-dithiobis(2-aminopropionic acid)

The compound was obtained following the procedure given in Example 18, starting from N-acetyl-L-cysteine and N-pivaloyl-L-cysteine.

Yield: 21%. Physical data: HPLC elution gradient: 50% A/15 min, 50 30% A/5 min, $R_f$=0.78 "BuOH/H$_2$O/HOAc=1/1/1). $^1$H-NMR (300 MHz, D$_2$O): δ 4.72 (2H, m, NCH), 3.35 (2H, m, CH$_2$), 3.04 (2H, m, SCH$_2$), 2.06 (3H, s, CH$_3$), 1.21 (9H, s, CCH$_3$). FAB-MS (m/z): 411 [MNa$_2$]$^+$, 389 [MNa]$^+$, 367 [MH]$^+$, 349 [MH-H$_2$O]$^+$.

Example 21

(R,R)-N,N'-di(2,2-dimethylpropionyl)-3,3'-dithiobis (2-aminopropionic acid)

The compound was isolated from the crude material of Example 20.

Yield: 15%. Physical data: HPLC elution gradient: 50% A/15 min, 50 30% A/15 min, 30%. A/isocratic (see Example 17 for solvents). TLC: $R_f$=0.88 "BuOH/H$_2$O/HOAc=1/1/1). $^1$H-NMR (300 MHz, D$_2$O): δ 4.72 (2H, dd, NCH), 3.37 (2H, dd, SCH$_2$), 3.06 (2H, dd, SCH$_2$), 1.21 (18H, s, CCH$_3$). FAB-MS (m/z): 431 [MNa]$^+$, 409 [MH]$^+$, 391 [MH-H$_2$O]$^+$.

Example 22

(R,R)-N-Acetyl-N'-pentanoyl-3,3'-dithiobis(2-aminopropionic acid)

This material was prepared as in Example 18, starting from N-acetylcysteine and N-pentanoylcysteine.

Yield: 23%. Physical data: HPLC elution gradient: 50% A/20 min, 50 25% A/5 min, 25% A/isocratic (see Example 17 for solvents). TLC: $R_f$=0.84 n-BuOH/$H_2O$/HOAc=1/1/1). $^1$H-NMR (300 MHz, $D_2O$): δ 4.70 (2H, m, NCH), 3.30 (2H, n, $SCH_2$), 2.99 (2H, m, $SCH_2$), 2.30 (2H, t, $COCH_2$), 2.04 (3H, s, $COCH_3$), 1.57 (2H, m, $CH_2$), 1.30 (2H, m, $CH_2$), 0.86 (3H, t, $CH_3$). FAB-MS (m/z): 389 [MNa]$^+$, 367 [MH]$^+$, 349 [MH-$H_2O$]$^+$.

Example 23

(R,R)-N,N'-dihexanoyl-3,3'-dithiobis(2-aminopropionic acid)

A suspension of 1 equiv. 3,3'-dithiobis(2-aminopropionic acid) dimethylester dihydrochloride in tetrahydrofuran (white slurry) was stirred and cooled to 0° C. To the reaction mixture was added 4 equiv. of N-ethyldiiso-propylamine and 2.2 equiv. of hexanoylchloride. The mixture was stirred for 4 hrs on an ice bath and the white precipitate of N-ethyldiisopropylammonium chloride was filtered off. The solvent was removed by evaporation under reduced pressure and the crude product was redissolved in dichlormethane. After washing with water, the organic phase was dried over sodium sulphate. Filtration and evaporation of the solvent gave crude (R,R)-N,N'-dihexanoyl-3,3'-dithiobis(2-aminopropionic acid) dimethylester, which was recrystallized from methanol/water and triturated with diethylether.

A white slurry (0.1M) of the above formed dimethylester and 0.5M sodium hydroxide in 10% methanol was stirred vigorously at room temperature. After about 48 hrs the pH of the clear solution was adjusted to 2, and the formed white precipitate of crude product was filtered off and recrystallized from acetone/hexane to give the title compound as white crystals.

Total yield: 28%. Physical data: Mp: 132°–135° C. $[\alpha]_D^{25}$:-164° (c=0.501, MeOH). $^1$H-NMR (300 MHz, DMSO-$d_6$), δ 8.22 (2H, d, NH), 4.49 (2H, m, CHN), 3.14 (2H, dd, $CH_2S$), 2.91 (2H, dd, $CH_2S$), 2.12 (4H, t, $CH_2CO$), 1.50 (4H, p, $CH_2CH_2CO$), 1.26 (8H, m, $(CH_2)_2$), 0.87 (6H, t, $CH_3$). Anal. Calcd for $C_{18}H_{32}N_2O_6S_2$: C, 49.5; H, 7.4; N, 6.4; S, 14.7. Found: C, 49.4; H, 7.2; N, 6.2; S, 14.3.

Example 24

(R,R)-N,N'-di(1-oxo-octyl)-3,3'-dithiobis(2-aminopropionic acid)

The compound was prepared according to the procedure described in Example 23, using octanoic acid chloride as the acylating agent.

The initially formed (R,R)-N,N'-di(1-oxo-octyl)-3,3'-dithiobis(2-aminopropionic acid) dimethylester was recrystallized from ethyl acetate and the title compound was recrystallized from acetone/heptane and triturated with diethylether to give white crystals.

Total yield: 20%; Physical data: Mp: 105°–107° C. $[\alpha]_D^{25}$:-147° (c=0.541, MeOH). $^1$H-NMR (300 MHz, DMSO-$d_6$), δ 8.18 (2H, d, NH), 4.48 (2H, m, CHN), 3.17 (2H, dd, $CH_2S$), 2.89 (2H, dd, $CH_2S$), 2.12 (4H, t, $CH_2CO$), 1.49 (4H, m, $CH_2CH_2CO$), 1.26 (16H, m, $(CH_2)_4$), 0.87 (6H, t, $CH_3$). Anal. Calcd for $C_{22}H_{40}N_2O_6S_2$: C, 53.6; H, 8.2; N, 5.7; S, 13.0. Found: C, 53.4; H, 8.5; N, 5.7; S, 12.6.

Example 25

(R,R)-N,N'-di(1-oxo-dodecanyl)-3,3'-dithiobis(2-aminopropionic acid)

The compound was prepared according to the procedure described in Example 23, using dodecanoic acid chloride as the acylating agent. The hydrolysis was carried out in 20% methanol.

The initially formed (R,R)-N,N'-di(1-oxo-dodecanyl)-3,3'-dithiobis(2-aminopropionic acid) dimethylester was recrystallized from ethyl acetate. The title compound was recrystallized from toluene/dichloromethane to give white crystals.

Total yield: 23%; Physical data: Mp: 110°–112° C. $[\alpha]_D^{25}$:-113° (c=0.507, MeOH). $^1$H-NMR (300 MHz, DMSO-$d_6$), δ 8.19 (2H, d, NH), 4.48 (2H, m, CHN), 3.15 (2H, dd, $CH_2S$), 2.89 (2H, dd, $CH_2S$), 2.11 (4H, t, $CH_2CO$), 1.49 (4H, m, $CH_2CH_2CO$), 1.25 (32H, m, $(CH_2)_8$), 0.87 (6H, t, $CH_3$). Anal. Calcd for $C_{30}H_{56}N_2O_6S_2$: C, 59.6; H, 9.3; N, 4.6; S, 10.6. Found: C, 59.2; H, 9.4; N, 4.6; S, 10.3.

Example 26

(S,S)-N,N'-di(2-methylpropionyl)-3,3'-dithiobis(2-aminopropionic acid)

Potassium carbonate (17.6 g, 127 mmol) was dissolved in 40 ml of water and 40 ml of methylene chloride under nitrogen. The solution was cooled (-10° C.) and 2-methyl propionoyl chloride (5.6 ml, 40 mmol) and D-cysteine hydrochloride monohydrate (8.7 g, 49.5 mol) was added quickly. The reaction mixture was stirred at room temperature for 4 hours, after which hydrochloric acid was added until the pH of the mixture became less than 1 according to lithmus paper. The aqueous layer was discarded and light petroleum (40°–60°) was added to the organic layer whereupon N-isobutyryl-D-cysteine precipitated as white crystals.

N-isobutyryl-D-cysteine (1 g, 5.2 mmol) was dissolved in 10 ml of methanol. Hydrogen peroxide (30%, 0.3 ml, 2.6 mmol) was added and the reaction mixture was stirred at room temperature for 6 hours. After evaporation of the solvent under reduced pressure, a white crystallised oil was obtained. Recrystallisation from ethyl acetate furnished the title compound as a white solid which was dried in vacuo.

Yield: 0.55 g (55%) Physical data: Mp 135°–137° C. $^1$H-NMR (300 MHz, DMSO-$d_6$) δ 8.16 (2H, d, NH) 4.47 (2H, m, CHN) 3.15 (2H, dd, $CH_2S$, J=14 Hz, 5 Hz) 2.93 (2H, dd, $CH_2S$, J=14 Hz, 9 Hz) 2.43 (2H, h, $CH(CH_3)_2$ J=7 Hz) 1.01 (12H, d, $CH_3$, J=7 Hz). $[\alpha]_D^{25}$=+167.6 (c=0.516, MeOH).

Example 27.

Formulation A

Tablet containing 10 mg of active substance per tablet:

Active substance 10 mg

Lactose 100 mg

Potato starch 50 mg

Polyvinylpyrrolidone 5 mg

Microcrystalline cellulose 15 mg

Magnesium stearate 1 mg

Formulation B

Direct compression tablet containing 5 mg of active substance per tablet:

Active substance 5 mg
Lactose, anhydrous 150 mg
Microcrystalline cellulose 50 mg
Colloidal silicon dioxide 1 mg
Magnesium stearate 2 mg If desired, the obtained tablets can be film coated with e.g. hydroxypropyl methylcellulose, hydroxypropyl cellulose or dimethylaminoethyl methacrylate methacrylic acid ester copolymer.

Formulation C

Solution for injection containing active substance 1 mg/ml

Active substance 1.0 mg
Sodium chloride 8.8 mg
Water for injection to 1 ml

Formulation D

Oral solution containing active substance 1 mg/ml

Active substance 1.0 mg
Sorbitol 150 mg
Glycerin 100 mg
Disodium edetate 0.5 mg
Preservative q.s.
Flavor q.s.
Water, purified to 1 ml Formulation E Powder aerosol giving 1 mg per dose The micronized active substance can be filled into a powder inhaler device e.g. Turbuhaler$^R$ giving 1 mg/dose.

Effects of the Compounds of the Invention in a Model of Delayed Type Hypersensitivity in the Mouse.

The property of the compounds of the invention to stimulate immune responses are illustrated by their efficacy in a model in the mouse of the delayed type hypersensitivity (DTH) reaction.

Both male and female Balb/c mice obtained from Bomhotsgaard (Denmark) and Charlie Rivers (England), were used at the weight of 18–20 gram. 4-ethoxymethylene-2-phenyloxazolone (OXA) was purchased from BDH (England) and served as an antigen in this test.

The mice were sensitized, Day 0, by epicutaneous application of 150 ul absolute ethanol-acetone (3:1) solution containing 3% OXA on the shaved thorax and abdomen. Treatment with the compound under examination, DiNAC (as a positive control) or vehicle (phosphate buffer, pH 7.0) was initiated by oral feeding immediately after sensitization and continued once to Day 6. Seven days (Day 6) after the sensitization both ears of all mice were challenged on both sides by topical application of 20 ul 1% OXA dissolved in olive oil. Ear thickness was measured prior to and 24 or 48 hours after challenge using an oditest spring calliper. Challenges and measurements were performed under light pentobarbital anaesthesia. The intensity of the DTH reactions was expressed according to the formula $T_{t24/48} - T_{t0}$ um nits, where t0 and t24/48 represent the ear thickness before and 24 or 48 hours after challenge, respectively, in individual test (T). The results were expressed as the mean+/−S.E.M. The level of significance between means of the groups was obtained by Student's two-tailed t-test. Table 1 shows representative results from 24 and 48 hours measurements expressed as % increase in ear thickness relative to that of the non-challenged reference ear. A figure of 100 thus indicates a doubled ear thickness.

TABLE 1

Immunostimulatory action

| R | $R^2$ | $R^3$ | % Increase, 24 h | | % Increase, 48 h | |
|---|---|---|---|---|---|---|
| | | | 0.03 μmol/kg | 3.0 μmol/kg | 0.03 μmol/kg | 3.0 μmol/kg |
| $COCH(CH_3)_2$ | $CH(CH_3)_2$ | $CH^3$ | 110*** | 92** | 17* | 27*** |
| $CO(n-C_5H_{11})$ | $n-C_5H_{11}$ | $CH_3$ | 73** | 86** | 51*** | 45*** |
| $CO(n-C_7H_{15})$ | $n-C_7H_{15}$ | $CH_3$ | 58*** | 52*** | 28** | 20* |
| $CO(n-C_7H_{15})$ | $n-C_7H_{15}$ | $C_2H_5$ | 49*** | 7 | 0 | 0 |
| $COC(CH_3)_3$ | $C(CH_3)_3$ | H | 14* | | 26* | 27* |
| $COCH(CH_3)_2$ | $CH(CH_3)_2$ | H | 17 | 18 | 27** | 62*** |
| $COCH_3$ | $C(CH_3)_3$ | H | 24* | 26* | 14 | 17* |
| H | $CH(CH_3)_2$ | H | 37** | 31*** | | |

*, , *: P < 0.05, 0.01, 0.001

We claim:

1. A method for the treatment of diseases resulting from a defect in the immune system in mammals, which comprises administration to a host in need of such treatment of an effective amount of a compound of the formula I:

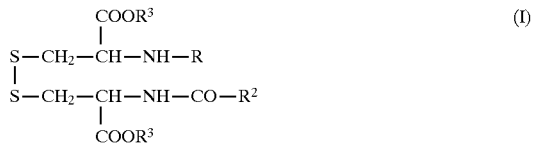

or a physiologically acceptable salt and/or a stereochemical isomer thereof in a pharmaceutically acceptable carrier, wherein R is hydrogen or a moiety —CO—$R^1$ wherein $R^1$ is methyl, ethyl, n-propyl, n-butyl, n-pentyl, n-hexyl, n-heptyl, n-octyl, n-nonyl, n-decyl, n-undecyl, iso-propyl, 1-methylpropyl, tert butyl, 3-methylbutyl or 2-methylbutyl; $R^2$ is methyl, ethyl, n-propyl, n-butyl, n-pentyl, n-hexyl, n-heptyl, n-octyl, n-nonyl, n-decyl, n-undecyl, iso-propyl, 1-methylpropyl, tert butyl, 3-methylbutyl or 2-methylbutyl; and $R^3$ is hydrogen, methyl, ethyl, propyl, isopropyl, butyl or isobutyl, provided that $R^1$ and $R^2$ are not simultaneously methyl and further provided that when $R^3$ is hydrogen, $R^1$ and $R^2$ are not simultaneously n-propyl or n-heptyl.

2. A method for stimulating the immune response in mammals which comprises internally administering to a host in need of such treatment a pharmaceutical preparation consisting essentially of an effective amount of an active compound of the formula I:

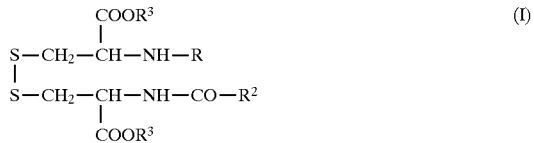

or a physiologically acceptable salt and/or a stereochemical isomer thereof in a pharmaceutically acceptable carrier, wherein R is hydrogen or a moiety —CO—$R^1$ wherein $R^1$ is methyl, ethyl n-propyl, n-butyl, n-pentyl, n-hexyl, n-heptyl, n-octyl, n-nonyl, n-decyl, n-undecyl, iso-propyl, 1-methylpropyl, tert butyl, 3-methylbutyl or 2-methylbutyl; $R^2$ is methyl, ethyl, n-propyl, n-butyl, n-pentyl, n-hexyl, n-heptyl, n-octyl, n-nonyl, n-decyl, n-undecyl, iso-propyl, 1-methylpropyl, tert butyl, 3-methylbutyl or 2-methylbutyl; and $R^3$ is hydrogen, methyl, ethyl, propyl, isopropyl, butyl or isobutyl, provided that $R^1$ and $R^2$ are not simultaneously methyl and further provided that when $R^3$ is hydrogen $R^1$ and $R^2$ are not simultaneously n-propyl or n-heptyl.

3. The method according to claims 1 or 2, wherein $R^3$ is methyl or ethyl.

4. The method according to claims 1 or 2, wherein $R^1$ and $R^2$ are isopropyl and $R^3$ is methyl.

5. The method according to claims 1 or 2, wherein $R^1$ and $R^2$ are n-pentyl and $R^3$ is methyl.

6. The method according to claims 1 or 2, wherein $R^1$ and $R^2$ are n-heptyl and $R^3$ is methyl or ethyl.

7. The method according to claims 1 or 2, wherein $R^1$ and $R^2$ are isopropyl.

8. The method according to claims 1 or 2, wherein $R^1$ and $R^2$ are tertbutyl.

9. The method according to claim 1, wherein the diseases are chronic bronchitis, asthma, rhinitis, diabetes, rheumatoid arthritis or malignant diseases.

10. The method according to claim 2, wherein the immune response is stimulated against chronic bronchitis, asthma, rhinitis, diabetes, rheumatoid arthritis or malignant diseases.

\* \* \* \* \*